(12) United States Patent
Bi

(10) Patent No.: US 10,416,059 B1
(45) Date of Patent: Sep. 17, 2019

(54) HIGH PRESSURE HIGH TEMPERATURE SPINNING DROP TENSIOMETER

(71) Applicant: Hongfeng Bi, Houston, TX (US)

(72) Inventor: Hongfeng Bi, Houston, TX (US)

(73) Assignee: Hongfeng Bi, Houston, TX (US)

(*) Notice: Subject to any disclaimer, the term of this patent is extended or adjusted under 35 U.S.C. 154(b) by 319 days.

(21) Appl. No.: 15/434,805

(22) Filed: Feb. 16, 2017

(51) Int. Cl.
*G01N 13/02* (2006.01)

(52) U.S. Cl.
CPC ..... *G01N 13/02* (2013.01); *G01N 2013/0241* (2013.01)

(58) Field of Classification Search
CPC ............... G01N 13/02; G01N 2013/0241
See application file for complete search history.

(56) References Cited

U.S. PATENT DOCUMENTS

| | | |
|---|---|---|
| 4,250,741 A | 2/1981 | Scriven, II et al. |
| 4,391,129 A * | 7/1983 | Trinh ............... G01N 29/036 |
| | | 250/573 |
| 4,644,782 A | 2/1987 | Joseph |
| 5,150,607 A | 9/1992 | Joseph et al. |
| 5,394,740 A * | 3/1995 | Schramm ............... G01N 13/02 |
| | | 73/64.48 |
| 9,869,624 B2 * | 1/2018 | Szabo ............... G01N 13/02 |
| 2018/0259499 A1 * | 9/2018 | Al-Yousef ............... E21B 43/20 |

FOREIGN PATENT DOCUMENTS

| | | | | |
|---|---|---|---|---|
| EP | 3090802 A1 * | 11/2016 | ............ | B01L 3/5021 |
| WO | WO-2012080536 A1 * | 6/2012 | ............ | G01N 13/02 |

* cited by examiner

*Primary Examiner* — John Fitzgerald

(57) ABSTRACT

A high pressure high temperature spinning drop tensiometer is capable of measuring interfacial tension under varied pressure and temperature conditions, which simulates those present in real petroleum reservoir. Measuring interfacial tension under real petroleum reservoir condition enables a selection of surfactants and other materials for adjusting the interfacial tension to be desired value for optimizing the enhanced oil recovery. The present invention mainly includes a pressure vessel comprising a pair of sight glasses. Two immiscible sample fluids are contained in a glass tube, which is carried by a tube holder rotated by a motor. A microscope and a light source sit on each side of sight glasses for analyzing the drop shape of the sample fluids under varied pressure and temperature conditions.

17 Claims, 2 Drawing Sheets

Figure 1:
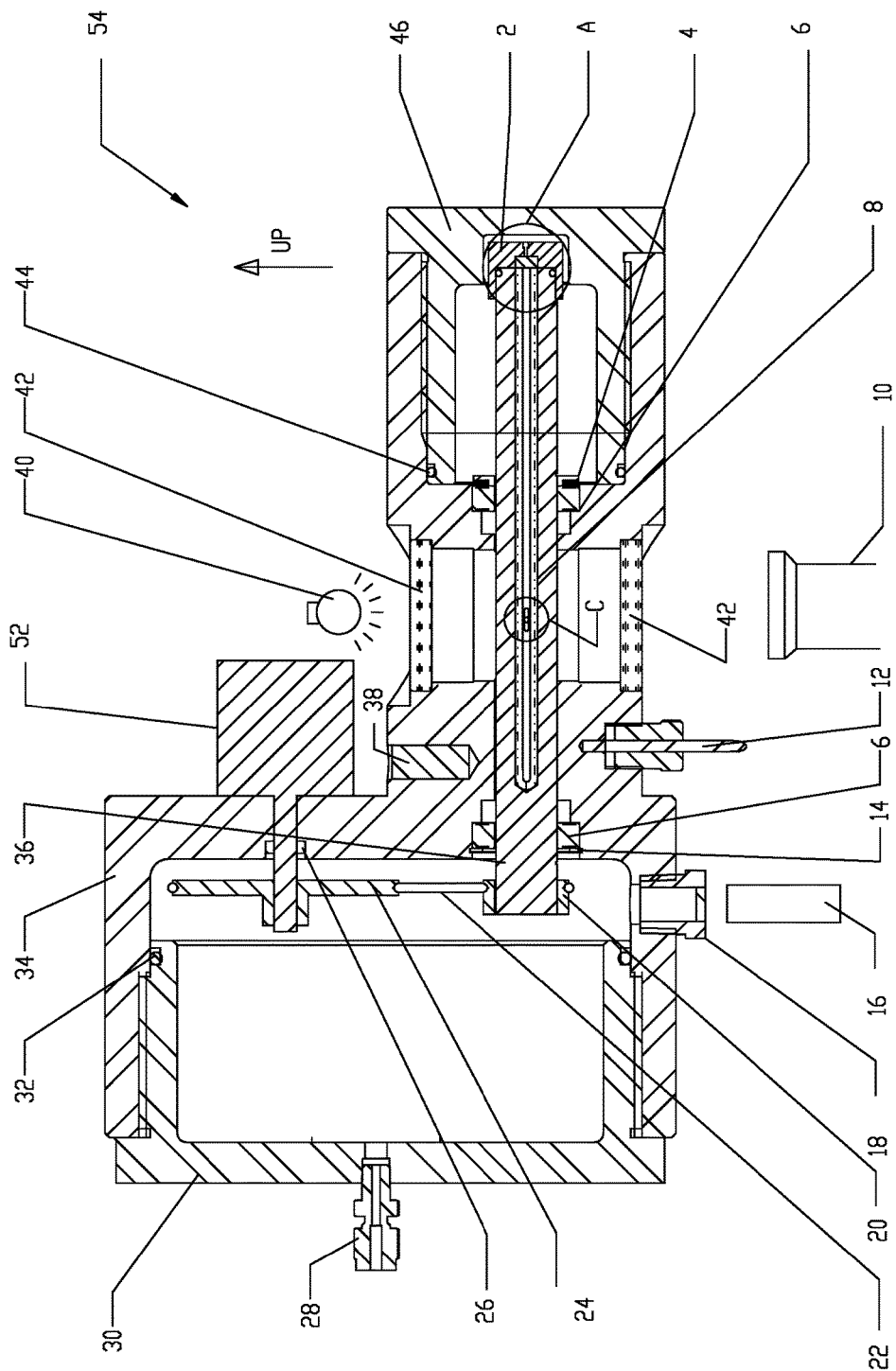

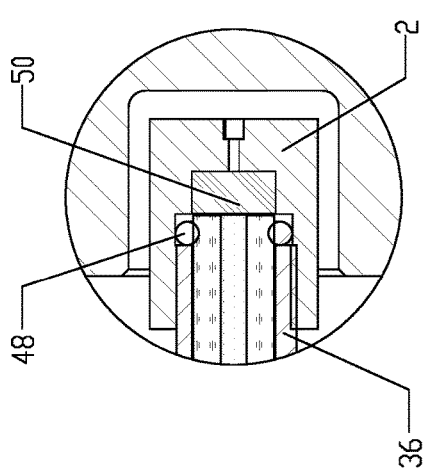
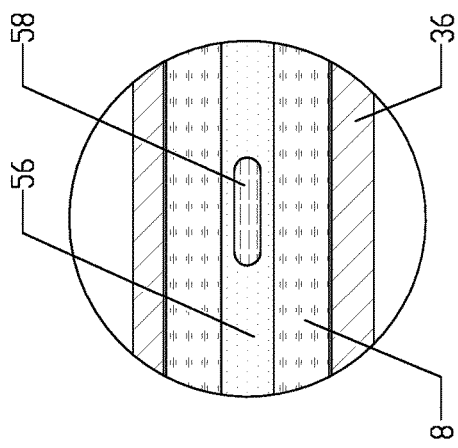
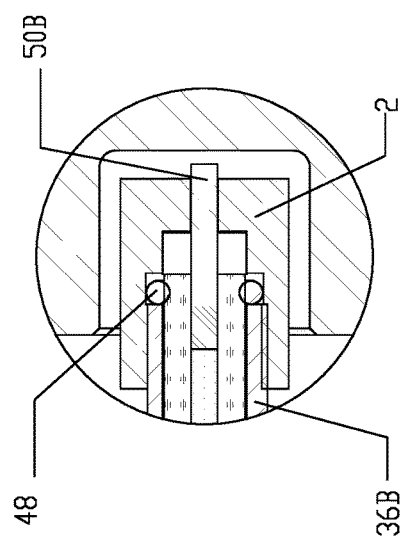

HIGH PRESSURE HIGH TEMPERATURE SPINNING DROP TENSIOMETER

BACKGROUND

Field of the Invention

The present invention pertains to a method and apparatus for determining interfacial tension between two immiscible fluids: liquid/liquid or gas/liquid by means of a droplet of the less dense fluid surrounded by the more dense fluid, both fluids are spinning together with a glass tube. This basic physical property of fluid interface is important to most fields of technological art in chemical solutions for enhanced oil recovery.

The invention pertains to measurement of interfacial tension but is especially advantageous for measurement of all magnitudes of interfacial tension less than 1 dyn/cm ($10^{-3}$ newton/meter) and is even more advantageous for measurement of interfacial tension less than $10^{-2}$dyn/cm ($10^{-5}$ newton/meter) and rotation speed need to be more than 10,000 rpm. It is also advantageous for interfacial tension measurement at pressure and temperature substantially different from ambient condition.

Description of Prior Art

Conventional methods of measuring fluid interfacial tension are the force method, the shape method, and several miscellaneous methods. The spinning drop technique is a shape method, which is used to measure low interfacial tension. U.S. Pat. No. 4,250,741 teaches an instrument for measuring interfacial tension between two fluids, which is based upon spinning drop technique, one of the conventional shape methods of the known art for measuring fluid interfacial tension. This invention includes a sample tube for containing the fluids and housing for enclosing the sample tube. A massive bearing housing contains a precision ground shaft and is connected to the sample tube. The shaft is rotated by a motor causing the sample tube to rotate at the same time. However, this instrument requires specially constructed equipment and parts. Furthermore, interfacial tension measurement requires a great deal of time and skill. Last but not least, this instrument cannot provide interfacial tension measurement under high pressure and high temperature conditions.

U.S. Pat. No. 4,644,782 introduces a method and device for measuring interfacial tension between two immiscible liquids. The device comprises a transparent tubular cylinder for receiving two liquids of different densities and a rod which is mounted on the longitudinal axis of the cylinder. The cylinder is sealed at both ends. The less dense liquid will form around the rod at an appropriate speed, and when steady state equilibrium is achieved by the liquids inside the cylinder, the diameter of the less dense liquid and the rotational speed of the cylinders are measured. However, this invention cannot provide interfacial tension measurement under high pressure and high temperature conditions.

U.S. Pat. No. 5,150,607 discloses an apparatus for measuring interfacial tension between two different polymers, under conditions which keep the polymers melted, and which cause the less dense polymer form a drop of a generally cigar shape. By measuring the diameter of the drop at desired angular velocities upper and lower bounds for interfacial tension can be determined. However, this invention cannot provide interfacial tension measurement under high pressure and high temperature conditions.

It is an object of this invention to provide a simple and robust construction that does not require sophisticated technology or expensive materials for high pressure high temperature interfacial tension measurement.

It is another object of this invention to provide a practical and affordable low maintenance device for accurately measuring surface or interfacial tension between two immiscible fluids without compromising its integrity and performance.

It is another object of this invention to provide a surface or interfacial tension measurement device which requires substantially less maintenance work than other designs yet meets industry standards of accuracy, repeatability, durability, and ease of cleaning.

SUMMARY OF THE PRESENT INVENTION

The high pressure high temperature spinning drop tensiometer used in the enhanced oil recovery area is capable of measuring interfacial tension between two immiscible fluids based on the spinning drop method. A glass tube is filled with two fluids of different densities and is sealed by a tube cap that comprises a rubber piston or other kind of elastomers. The glass tube is placed inside of a tube holder which is mounted horizontally between two bearings and is driven to rotate around the longitudinal axial direction of the tube holder. A droplet of less dense fluid can be viewed through a sight glass and shape of the drop can be measured by a microscope.

DRAWING FIGURES

Other objects, features and advantages will be apparent from the following detailed descriptions of embodiment taken in conjunction with accompanying drawing in which: FIG. 1 is a cross-sectional view of high pressure high temperature spinning drop tensiometer according to embodiment of the present disclosure. FIG. 2A is a cross-sectional view of part A in FIG. 1. FIG. 2B shows an alternative construction of FIG. 2A. FIG. 3 is a cross-sectional view of part C in FIG. 1.

| REFERENCE NUMERALS IN DRAWINGS | |
| --- | --- |
| 2 tube cap | 4 bearing retainer |
| 6 bearing | 8 glass tube |
| 10 microscope | 12 thermocouple |
| 14 retaining ring | 16 optical sensor |
| 18 sight window | 20 small pulley |
| 22 belt | 24 large pulley |
| 26 dynamic seal | 28 fitting |
| 30 large plug | 32 o-ring |
| 34 pressure vessel | 36 tube holder |
| 38 heater | 40 light source |
| 42 sight glass | 44 o-ring |
| 46 small plug | 48 o-ring |
| 50 rubber block | 50B rubber piston |
| 52 motor | |
| 54 high pressure high temperature spinning drop tensiometer | |
| 56 sample I | 58 sample II |

DETAILED DESCRIPTION OF THE PREFERRED EMBODIMENTS

Embodiments disclosed herein are related to an apparatus to measure interfacial tension between two immiscible fluids. More specifically, embodiments disclosed herein are related to interfacial tension measurement under high pressure and high temperature condition that is a very useful application in Enhanced Oil Recovery (Tertiary Oil Recovery).

Referring to FIG. 1, a high pressure high temperature spinning drop tensiometer 54 includes a pressure vessel 34 comprising a pair of sight glass 42 for viewing the experiment. A glass tube 8 is placed in a tube holder 36, which is supported by a pair of bearing 6 in pressure vessel 34. A retaining ring 14 and a bearing retainer 4 are used to prevent tube holder 36 from sliding under high speed rotation. In FIG. 2A, a sample I 56 and a sample II 58 are contained in glass tube 8 sealed by a tube cap 2.

In FIG. 1, a motor 52 and a dynamic seal 26 are installed on pressure vessel 34. A large pulley 24 and a small pulley 20 are installed on the shaft of motor 52 and tube holder 36 respectively. A belt 22 is used to connect large pulley 24 and small pulley 20. Motor 52 drives tube holder 36 to rotate through belt 22. An optical sensor 16 is used to monitor the rotation speed of glass tube 8 through a sight window 18. Large pulley 24 and small pulley 20 can be replaced with gears of different sizes. Due to the different sizes of large pulley 24 and small pulley 20, a relative low rotation speed of motor 52 can generate high rotation speed of tube holder 36. Thus dynamic seal 26 can work within its designed lower speed limit, while generating very high speed on tube holder 36. A small plug 46 with an o-ring 44 is screwed to the right end of pressure vessel 34 to provide an access and seal to tube holder 36. A large plug 30 with an o-ring 32 is attached to the left end of pressure vessel 34 to provide an access to large pulley 24.

Temperature control is provided by a heater 38, and a thermocouple 12 is used to measure temperature inside of pressure vessel 34. A light source 40 locates on one side of sight glass 42, and a microscope 10 is positioned on the opposite side of sight glass 42. They are used to observe and measure the diameter of the droplet of sample II 58 inside of glass tube 8. A pressurization media, such as nitrogen, helium or oil, is introduced into pressure vessel 34 through a fitting 28.

FIG. 2A and FIG. 2B show two types of structures that could be used in glass tube 8 for preventing sample I 56 from escaping glass tube 8 due to high speed rotation and thermal expansion. In FIG. 2A, a rubber block 50 is installed in tube cap 2 and pressurization media pushes rubber block 50 against glass tube 8 to provide sealing. Alternatively, FIG. 2B shows that a small rubber piston 50B is inserted into glass tube 8 to provide sealing. Rubber piston 50B can move inward along the horizontal axial direction of glass tube 8 by pressurization media. Or, rubber piston 50B can move outward along the horizontal axial direction of glass tube 8 due to thermal expansion of sample I 56.

FIG. 3 is a cross section view of part C shown in FIG. 1. A droplet of sample II 58 is surrounded by sample I 56. The droplet of sample II 58 will be elongated under high speed rotation, and the interface between sample I 56 and sample II 58 is captured by microscope 10.

OPERATION OF THE PREFFERD EMBODIMENTS

Prefill glass tube 8 with sample I 56 first, then inject a drop of sample II 58 near the middle of glass tube 8. Insert glass tube 8 into tube holder 36. Put rubber block 50 and o-ring 48 into tube cap 2 before screwing tube cap 2 onto tube holder 36. Attach o-ring 44 to small plug 46 before screwing it onto pressure vessel 34.

Install heater 38 and thermocouple 12 on pressure vessel 34. Fitting 28 is used to connect pressurization media. Motor 52 can drive tube holder 36 and glass tube 8 to rotate through belt 22. Microscope 10 and light source 40 sit on each side of sight glass 42 for optical observation of experiments. Computer based software is used to analyze the droplet shape and contact angle of sample II 58 under varied pressure and temperature from ambient condition.

Conclusion, Ramifications, and Scope

A ramification of the preferred embodiment is that pressure vessel 34 which can be shaped like a square, a cylinder, or other shapes.

Another ramification of the preferred embodiment is that large pulley 24 and small pulley 20 can be replaced with a pair of large gear and small gear.

Another ramification of the preferred embodiment is that glass tube 8 can be made of other materials as long as they are transparent to the light waves emitted by light source 40.

Another ramification of the preferred embodiment is that glass tube 8 can be shaped like a square, a cylinder, or other shapes.

Another ramification of the preferred embodiment is that rubber piston 50B can be other kinds of elastomers.

It will be now be apparent to those skilled in the art that other embodiments, improvements, details, and uses can be made consistent with letter and spirit of the foregoing disclosure and within the scope of this patent, which is limited only by the following claims, construed in accordance with the patent law, including, the doctrine of equivalents.

Objects and Advantages

From the description above, a number of advantages of present invention become evident:

a. Very economically measuring interfacial tension between immiscible fluids by a spinning drop technique under elevated temperature and pressure conditions.

b. Due to the limited number of components and configuration, the current invention is easy to manufacture, operate and requires low maintenance.

Further objects and advantages of my invention will become apparent from a consideration of the drawing and ensuing descriptions.

The invention claimed is:

1. A high pressure high temperature spinning drop tensiometer comprising:
   a) a glass tube for receiving at least two different sample fluids with different densities,
   b) a rotatable tube holder rotates with said glass tube along a longitudinal axis of said glass tube,
   c) a pressure vessel for receiving said glass tube and said tube holder,
   d) a pressurization media is applied to pressurize said pressure vessel,
   e) a pair of transparent sight glasses on said pressure vessel for observing said glass tube,
   f) a means for measuring geometries of the interface between said sample fluids,
   g) a larger pulley located inside of said pressure vessel rotated by a rotatable shaft,
   h) a smaller pulley rotates with said tube holder,
   i) a belt connects said larger pulley to said small pulley.

2. The high pressure high temperature spinning drop tensiometer of claim 1 further comprising a motor mounted on said pressure vessel rotates said large pulley.

3. The high pressure high temperature spinning drop tensiometer of claim 1 wherein said larger pulley is a smooth pulley.

4. The high pressure high temperature spinning drop tensiometer of claim 1 further comprising a means to control rotation speed.

5. The high pressure high temperature spinning drop tensiometer of claim 1 further comprising a tube cap for sealing glass tube.

6. The high pressure high temperature spinning drop tensiometer of claim 1 wherein said pressurization media is a gas.

7. The high pressure high temperature spinning drop tensiometer of claim 1 wherein said pressurization media is a liquid.

8. The high pressure high temperature spinning drop tensiometer of claim 1 further comprising a means to provide temperature control in said pressure vessel.

9. The high pressure high temperature spinning drop tensiometer of claim 1 further comprising an optical sensor to provide accurate measurement of rotational speed of said tube holder.

10. A high pressure high temperature spinning drop tensiometer comprising:
   a) a glass tube for receiving at least two sample fluids with different densities,
   b) a rotatable tube holder rotates with said glass tube along a longitudinal axis of said glass tube,
   c) a pressure vessel for receiving said glass tube and said tube holder,
   d) a pressurization media is applied to pressurize said pressure vessel,
   e) a pair of transparent sight glasses on said pressure vessel for observing said glass tube,
   f) a means for measuring geometries of the interface between said sample fluids,
   g) a larger gear located inside of said pressure vessel and rotated by a rotatable shaft,
   h) a smaller gear rotates with said tube holder.

11. The high pressure high temperature spinning drop tensiometer of claim 10 further comprising a motor mounted on said pressure vessel rotates said large gear.

12. The high pressure high temperature spinning drop tensiometer of claim 10 further comprising a means to control rotation speed.

13. The high pressure high temperature spinning drop tensiometer of claim 10 further comprising a tube cap for sealing glass tube.

14. The high pressure high temperature spinning drop tensiometer of claim 10 wherein said pressurization media is a gas.

15. The high pressure high temperature spinning drop tensiometer of claim 10 wherein said pressurization media is a liquid.

16. The high pressure high temperature spinning drop tensiometer of claim 10 further comprising a means to provide temperature control in said pressure vessel.

17. The high pressure high temperature spinning drop tensiometer of claim 10 further comprising an optical sensor to provide accurate measurement of rotational speed of said tube holder.

\* \* \* \* \*